United States Patent [19]

Benckhuijsen

[11] 4,336,807
[45] Jun. 29, 1982

[54] WAISTCOAT FOR THERAPEUTIC TREATMENT

[75] Inventor: Gerrit J. Benckhuijsen, Schaan, Liechtenstein

[73] Assignee: Temova Etablissement, Schaan, Liechtenstein

[21] Appl. No.: 151,617

[22] Filed: May 20, 1980

[30] Foreign Application Priority Data

May 21, 1979 [CH] Switzerland .................. 4739/79

[51] Int. Cl.³ ............................................ A61N 00/00
[52] U.S. Cl. .................................. 128/379; 128/380; 128/DIG. 23
[58] Field of Search ............ 128/379, 380, DIG. 23; 2/98, 99, 100, 131, 132

[56] References Cited

U.S. PATENT DOCUMENTS

| 837,143 | 11/1906 | Starr | 2/98 |
|---|---|---|---|
| 2,417,271 | 3/1947 | Snyder | 2/98 |
| 2,803,834 | 8/1957 | McClung | 128/DIG. 23 |
| 3,783,879 | 1/1974 | Stalder | 128/570 |
| 3,810,466 | 5/1974 | Rodgers | 128/DIG. 23 |
| 3,833,938 | 9/1974 | Shweid | 2/98 |
| 3,921,626 | 11/1975 | Neel | 128/DIG. 23 |
| 4,232,663 | 11/1980 | Newton | 128/DIG. 23 |

Primary Examiner—Robert W. Michell
Assistant Examiner—C. W. Shedd
Attorney, Agent, or Firm—Cushman, Darby & Cushman

[57] ABSTRACT

Therapeutic waistcoat for the treatment of ailments in the cervical and neck-arm region, e.g. cervical syndrome, omarthrose, periarthritis. The waistcoat tightly encloses the entire upper part of the body and has a collar part at least twice as long as the neck. The collar folds down to form a stiff collar; if desired, an additional neck support may be inserted into it. With or without additional neck support, the collar is dimensioned in a way to assure contact pressure by the collar part on the entire neck region up to the jaw and the base of the skull. The fabric of the waistcoat, including the collar part, consists of an electrostatically active knit made of a mix of polyvinyl chloride and acrylic fibres. The supporting effect applied in the neck region in combination with the increased heat effect caused by the contact pressure results in a therapeutic effect in the cervical range which radiates to the areas of the shoulder and elbow joints.

4 Claims, 3 Drawing Figures

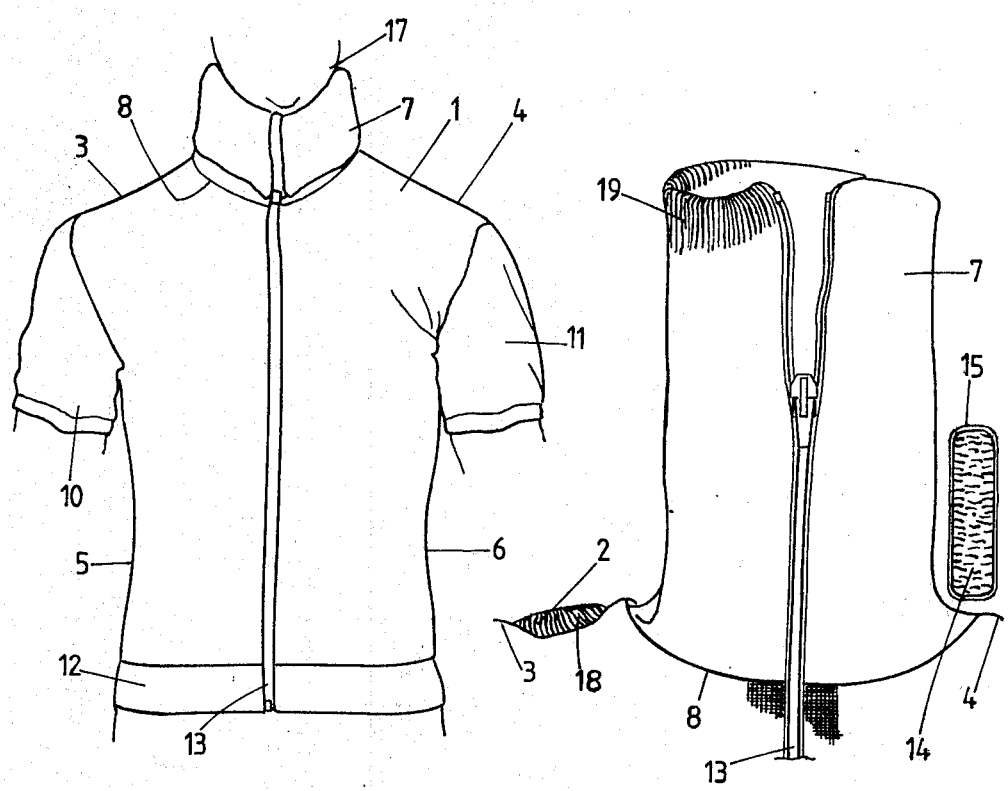
FIG. 1
FIG. 3
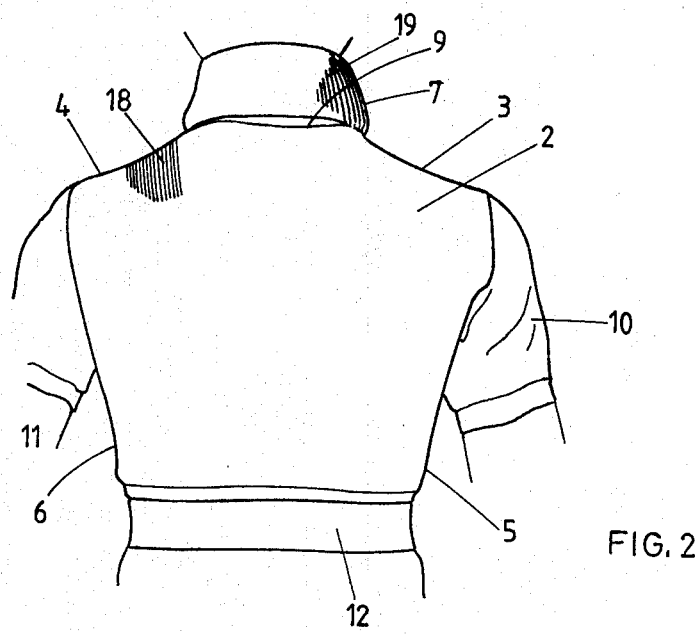
FIG. 2

WAISTCOAT FOR THERAPEUTIC TREATMENT

The present invention relates to a waistcoat intended for therapeutic treatment consisting of an elastic, electrostatically chargeable textile fabric which fits close to the body, with front and back parts joined at the shoulder and side lines of the body, with an elastic band at the lower edge, as well as sleeves, and a separating fastener running along the front and the elastic band.

Such waistcoats have a healthy effect and are therefore on the market as a so-called health-wear. In the present case, the therapeutic effect consists mainly in the thermal effect achieved by the static electricity of the textile fabric applied close to the skin. Consequently, such waistcoats are primarily used to avoid or to alleviate colds, rheumatism, arthrosis and back-aches. Another type of waistcoat, for instance, consists merely of a back part and short-sleeved, elastic shoulder parts and is supposed to cure trouble of the shoulder joint as a so-called shoulder joint bandage. It is a proven fact, though, that those waistcoats are only to a limited extent or not at all effective in the therapy of serious ailments such as degenerative changes, irritations and trouble due to overstrain of the shoulder-arm region, e.g. shoulder/arm syndrome, omarthritis, omarthrose, periarthritis humeroscapularis and others where experience has shown that such external treatment is of minimal effectiveness.

Another, well-known ailment on the upper part of a patient's body is a painful condition in the cervical area, perhaps a cervical syndrome. Although so-called cervical collars or neck supports are being used in the therapy of injuries of the cervical vertebrae and the upper spinal column, but their efficiency is limited exclusively to such injuries, and no further use is made of cervical collars as a means of therapy or else without success in practice.

Swiss Patent Nos. 514.299 and 530.179 held by the applicant already describe a therapeutic waist support and hip girdle which alleviates pain and has a healing effect in particular on patients with kidney trouble and spinal column complaints. It is well known that functional disorders often appear simultaneously in these diverse regions. The surprising finding with that girdle was that a healing effect is achieved simultaneously for both ailments with a girdle which produces both warmth due to an electrostatic charge as well as a supporting action due to stiffeners. The healing action of this girdle is apparent from the examples given in the corresponding Austrian Patent No. 329.175. It was further found that the healing effect of such a girdle is only achieved when a knitted textile fabric made of polyvinyl chloride and acrylic fibres is used.

Based on the extensively proven curative effects of this therapeutic girdle we had grounds to assume that the simultaneous treatment of the above-named two pain spots in the shoulder and cervical regions might possibly improve chances of an external therapeutic treatment which had heretofore been little successful.

The present invention has the objective to produce a therapeutic waistcoat, based on the above findings, which will effectively cure or alleviate the above-mentioned disorders and pains of the shoulder-arm-region.

This objective is achieved by a waistcoat as herein described, characterized by a collar issuing from the front and back parts, at least twice as high as and covering the neck, by a knit textile fabric consisting of a mixture of long, nonhydroscopic polyvinyl chloride fibres and acrylic fibres, spun on a worsted basis, and suitable for generating static electricity.

by a collar, front and back parts, each consisting of a double layer of the textile fabric wherein the inner layer fits close to the skin, both layers movable by sections in relation to each other, with a sufficiently large mesh width to allow evaporation of skin moisture, at least in the collar and back parts.

by a collar part designed in such a way as to provide a stiff support once the top half is folded down onto the lower half and at the same time the inner layer of the textile fabric adheres to the skin of the neck, jaw and occipital regions exerting pressure, and wherein a pocket for a neck support is contained between the lower and the folded-over parts.

Hereinafter, the invention will be explained in detail for some embodiments by the enclosed drawings.

FIG. 1 shows a simplified representation of a longer waistcoat seen from the front, FIG. 2 shows a simplified representation of a shorter waistcoat seen from the back, FIG. 3 shows a schematic drawing of an enlarged view of the collar part of the waistcoat, according to FIGS. 1, 2, as well as a sectional view of the neck support.

As is apparent from FIGS. 1 to 3, the waistcoats consist of front and back parts 1 and 2, respectively, joined along the shoulder lines 3, 4 and along the side lines of the body 5, 6. Since the only difference between the waistcoats in FIGS. 1 and 2 consists in their respective lengths, but they are otherwise identical regarding structure and design, the same reference marks are being used in both FIGS. 1 and 2. The waistcoat has a collar part 7 as shown in FIG. 3. The collar part 7 is attached to the rounded necklines 8 or 9, respectively, of the front and back parts 1,2 below the base of the neck. In the areas of the shoulder lines 3, 4, the front and back parts 1,2 extend to the shoulder rounding where in this particular example the short sleeves 10, 11 are attached. At the lower edge of the front and back parts 1,2, an elastic band 12 hugs the body and avoids upward slipping of the waistcoat. The waistcoat which opens preferably in the front is held together by a separating fastener 13, e.g. a zipper running through the band 12, the front part 1 and the collar part 7. Consequently, the waistcoat completely encloses the entire upper part of the body, including the neck.

One of the essential features of the waistcoat is its collar part 7 according to FIG. 3 wherein the neck support 14, further described hereinafter, will only be included optionally. The collar part 7 is about twice as high as the neck of an average person and it is designed for the top, excess part to fold down onto the lower part, as indicated in FIGS. 1 and 2. Since the knit textile fabric used for the collar part 7 has great transverse elasticity, the folded down collar part 7 exerts considerable pressure on the neck of the wearer which is desirable for achieving the corresponding therapeutic effect. The design of the collar part 7 differentiates the present therapeutic waistcoat from regular apparel with so-called turtle-necks since the type of knit and the dimensions of the latter have to guarantee a minimum of resistance to movements in all directions. In contrast thereto, the folded-down collar part 7 is meant to provide a stiff collar which supports the chin and keeps the cervical column from bending too much to the sides. If a stronger supporting action is desired, an additional stiff neck support 14 may be introduced into the pocket created by the folded-down upper and the lower parts of collar part 7, as will be described in detail further on. Or else, supporting elements, e.g. elastic, reinforcing strips or support rods may be inserted at least into the lower half of collar part 7. Unlike garments with regular turtle-necks, the collar part 7 of the present waistcoat is so long that the stiff collar produced by folding down the top reaches all the way up to the jaw 17.

The collar part 7 is folded down into a stiff collar, either with or without neck collar 14, by its design as described above achieves two essential therapeutic effects: One of them is its supporting action which reduces rash turns of the head and body in a manner to spare the shoulder/arm and cervical regions. The second fundamental action consists in the fact that it acts as a pressure agent which maintains a certain, constant contact pressure between the skin of the patient's neck region and the inner layer of the textile fabric of neck part 7 touching it. It is well known that such contact pressure is conducive to warmth with an electrostatically active textile material such as that of collar part 7. Since the stiff collar reaches up to the level of the jaw 17 and in the back up to the occiput, the proper skin area up to the base of the skull is fully exposed to this increased warmth under pressure. Consequently, the temperature in the skin areas of the throat and the neck is constantly increased on the one hand, something not to be achieved merely by wearing a regular turtle-neck pullover, and on the other hand the electrostatic charges provide healing stimulation.

The front and back parts 1, 2, as well as the sleeves 10,11 of the waistcoat are made of the same textile fabric generating static electricity as the collar part 7. Testing of the suitable, electrostatically active textile fabrics has shown that the most effective therapeutic action is achieved by a knit material consisting of long polyvinyl chloride fibres, spun on a worsted basis, with an added share of acrylic fibres. One of the preferred types of knit fabrics contains between 80 and 90, preferably 85% of polyvinyl chloride fibres and the remainder of acrylic. Both are so-called long staple fibres with a fineness in the range of 20 to 3 denier which are occasionally called polyvinyl chloride rayon. Among this class of fibres we also find fibres of postchlorinated PVC and of vinyl chloride acetate copolymers. As is well-known, these non-hygroscopic synthetic fibres generate an electrostatic charge when the textile fabric is moved against the skin which in turn causes a sense of warmth on the corresponding skin areas which is practically independent of the ambient temperature and is constantly maintained by further movements, with an added temperature increase in the neck region, as described above.

Furthermore, the therapeutic effect of the waistcoat is increased by the special structure of the textile fabric. As illustrated by FIGS. 1 and 2, the front and back parts 1, 2 adapt perfectly to the body shapes. This adaptability is the result of a longitudinal structure 18 knit into the textile fabric of the back part 2, as indicated in FIG. 2, which exerts an elastic pull in transverse direction of the waistcoat. Similarly, the collar part 7 also has a longitudinal structure to make it fit elastically to the neck region. It is a particular advantage that all textile parts of the waistcoat, i.e. front and back parts 1,2, sleeves 10, 11 as well as the collar part 7 consist of a double layer of the textile fabric. This double layer is discernible in FIG. 3 at the top edge of the collar part 7 from the flow of the longitudinal structure 19. The inner layer of the textile fabric is in direct contact with the skin, and the friction against the skin generates an electrostatic charge. This is increased by the outer layer of the textile fabric which rubs against the inner layers. The mesh width of the textile fabric is sufficient to allow evaporation of the skin moisture caused by the thermal effect through both layers, thereby avoiding the unpleasant feeling of a sticky textile fabric during wear and in particular avoids the rapid discharge or reduction of the electrostatic charge. The electrostatic charges generated by the double-layer textile fabric which may reach up to 30'000 volts, do not only cause a temperature increase but as well a stimulating effect on the skin on the inflamed tissues below it. To achieve high electrostatic charges, the textile fabric ought to be as closely knit as possible, but on the other hand it still ought to have a sufficiently large mesh width.

It was found that all the requirements regarding structure and type of knit of the textile fabric of the separate parts of the waistcoat were best met by using a fine rib-knit for the back part 2 and collar part 7 and an interlock knit for the front part 1, according to the following specifications: The fine rib-knit was knitted with the above-mentioned, 2, 5 to 4 den. synthetic fibre on a STIBBE circular knitting machine, using 10 needles on 2 cm. The number of stitches was 20 stitches/2 cm in length and 14 stitches/2 cm in width, the number of stitches 70/cm$^2$ and the weight 160 g/m$^2$. In general, the most effective range of stitches for the fine rib-knit was found to be 18–25/2 cm in length and 12–20/2 cm in width and 100–400 g/m$^2$ proved to be the preferred weight range. Other circular knitting machines may also be used, as well as straight knitting machines, since the double-layer parts may both be knitted as a hose and folded or knit flat and sewed together. For the front part 1 to be made as an interlock knit, the preferred type is made with 16 needles on 2 cm, the weight of the yarn being 50'000 m long/kg, the number of stitches 25/2 cm in length and 26/2 cm in width and the weight of the fabric 150–400 g/m$^2$.

As mentioned above, it is a good idea to use the pocket created by folding down the top excess part of collar part 7 to insert a neck support 14 in order to give added stiffness to the collar part 7. An oblong strip of a resilient but dimensionally stable material with a self-adhesive, adjustable stick fastener of a well-known type serves as a neck support 14 and permits to adapt the neck support 14 to varying neck widths. The main requirement to be met by the material of the neck support 14 is to let air pass unhindered. This air permeability is necessary to let the skin moisture exuded under the lower, double-layer of the neck part 7 evaporate through the neck support 14. Otherwise, the considerable skin moisture exuded in the neck region due to the warmth would remain there and produce a sense of cold, in addition to jeopardizing the generation of an electrostatic charge. Generally, these specifications for the material of the neck support 14 are met by a body of the polyurethane-foam group since its open pores let air and humidity pass through and it has an elastic dimensional stability which assures polydirectional pressure by the neck support 14 against the lower part of collar part 7. The foam-body of the neck support 14 is, e.g. 1,5–2 cm thick and weighs 40 kg/m$^3$.

It is an advantage to cover the neck support 14 by a slip-cover permeable to air (15), preferably made of the same, electrostatically active type of fabric as the collar part 7. This increases the electrostatic charge at least of the lower part of the collar part 7 by friction against the slip-cover 15. It is also feasible to use several layers of the fabric as a slip-cover. In addition, the neck support may contain built-in stiffening rods if the ailment, e.g. an injury of the cervical vertebrae calls for it. Instead of providing for a separate neck support 14, it is also possible to integrate a piece of polyurethane foam into the collar part 7 as a support.

The present therapeutic waistcoat with a neck support 14 as described above replaces the traditional cervical collar which is neither porous nor consists of any electrostatically chargeable materials, whose effect is therefore purely acting as a support but shows none of the therapeutic effects described above. It is not recommendable, either, to use a cervical collar of traditional design in the pocket of the collar part 7 since the lack of porosity of these cervical collars may impair the evaporation of moisture.

When testing the present waistcoat as a therapeutic means to alleviate the ailments and aches mentioned above, a surprising curative effect and alleviation of pain was proven. Since such a curative effect had not been obtained with the previously known waistcoats, it is evident that the cause of the therapeutic effectiveness consists in the design of the vest according to the present invention, both in the neck region as well as in the shoulder area. It seems that the suppporting action in the neck region in combination with the substantial temperature increase due to the heat effect and the electrostatic stimulation of the skin results in an additional, unforeseeable therapeutic effect which also radiates to the more removed body areas, namely the shoulder and the elbow joints. This seems to be due to the mutual nervous, vasal and lymphatic influences of the cervical and the shoulder-arm-regions. It is an essential point that neither the supporting action nor the heat effect alone produce the therapeutic effect, but only a combination of the two in the presence of high electrostatic charges.

Based on our experience, the waistcoat according to the present invention is therapeutically effective with
  cervicobrachial syndrome in the broadest sense
  chronic, subchronic and acutely painful stiff shoulder or rheumatic disorders of soft tissues in the cervicoscapular region,
  cervical syndrome with pain radiating to the segments or with acute symptoms of a stiff neck,
  impairment of movements due to pain.
  omarthrose
  periarthritis humeroscapularis.

The longer version of the waistcoat according to FIG. 1 may also be applied for disorders in the spinal column and the chest regions.

If desired, the waistcoat may be supplied with buttons instead of the zip fastener as a separating fastener 13. The waistcoat may come in colours matching the skin, the underwear or the upper garments. Basically, all synthetic fibres suitable for generating static electricity may be used for knitting the textile fabric. Let us mention that the waistcoat as described above and regardless of its therapeutic objective, offers a further, considerable advantage to the wearer. Whereas up to now a cervical collar marks both female as well as male wearers immediately as patients, with its corresponding, substantial, psychological strain in their professional and private lives, the present therapeutic waistcoat looks like a regular, handsome garment with a so-called turtle-neck, and this impression is further helped by the possibility of dieing the waistcoat in various fashionable hues.

The effectiveness of the present invention has been tested and proven as shown by the following example which is an excerpt from an expert's opinion. The term VIBROSTATIC-shoulder joint bandage mentioned therein refers to the present waistcoat and VIBROSTATIC is a registered trademark owned by the applicant.

EXAMPLE (Dr, D.v.A., MD, Klinik und Insitut für Physikalische Therapie Nürnberg)

The Vibrostatic ®-shoulder joint bandages, purpose-built and with a turtle-neck attached were applied by us in suitable cases with clinical syndromes.

The effect on cervical syndromes with painful stiff shoulders which resisted therapy and are known to be difficult to treat was astonishing. More than others, these patients often complain about increased sensitivity to temperature. Whereas the previous treatments had only achieved an alleviation by high doses of medication or intra- and/or periarticular injections, the constant wearing of the Vibrostatic ®-shoulder joint bandage with the cervical collar resulted in a rapid improvement of pain, objectively in improved mobility in the cervical vertebrae-shoulder region and in the shoulder joint, above all in a reduction of tone of the hypertonic muscles affected in the segments of the intermediate and lower cervical vertebrae-shoulder range. Even the mostly discrete but subjectively all the more troublesome neurological concomitant phenomena of an initial hyperpathia, paresthesias all the way to an objectively provable loss of strength were unequivocally improved and with impressive speed when compared to conventional methods.

It is true that extending measures-in the clinical domain also as a permanent measure-and hour-long extensions by Glisson's sling or by suitable cervical collars were also applied. I hereby wish to attribute the striking success with the Vibrostatic ®-shoulder joint bandage including the Vibrostatic ®-cervical collar to the electrophysical properties described above and herein the high degree of heat insulation and the water-(perspiration)repellent property of the fibre are surely playing a decisive, albeit not easily quantifyable role.

I claim:

1. A waistcoat for therapeutic treatment adapted to closely fit the neck, shoulders and at least the upper trunk of a wearer and having front and back parts joined at the shoulder and side lines of the trunk, an elastic band at the lower edge, sleeves, a separating fastener along the front, and a collar part extending upward from the front and back parts, characterized by:
  being made of elastic knitted textile fabric comprising a mixture of long, non-hygroscopic polyvinyl chloride fibres and acrylic fibres spun on a worsted basis and suitable for generating static electricity on frictional movement against the skin of a wearer;
  the collar, front and back parts each comprising at least a double layer of the fabric wherein the inner layer fits close to the skin, the layers are movable in sections in relation to each other, and at least the collar and back parts having a mesh sufficiently large to allow evaporation of skin moisture of a wearer;

the collar part being at least twice as high as and covering the neck of a wearer and designed in such a way as to provide a stiff support for the neck when the top half is folded down onto the lower half while at the same time the inner layer of the textile fabric adheres to the skin of the neck, jaw and occipital region and the folded collar part exerts pressure on the neck region, and a pocket for a neck support is provided between the folded down upper and lower halves.

2. A waistcoat according to claim 1 including a removable neck support adapted to be located in the pocket, as long as the neck of a wearer, and made of a dimensionally stable, resilient strip of material made of polyurethane foam permeable to air.

3. A waistcoat according to claim 2 including a complete cover for the strip of material comprising the same knitted textile fabric as the other parts of the waistcoat.

4. A waistcoat according to claim 1 wherein the length of the collar is such that folding over the top half creates a folded edge which fits close to the mandibular region.

* * * * *